United States Patent [19]

Ogle, II

[11] Patent Number: 4,834,716

[45] Date of Patent: May 30, 1989

[54] PROTECTED CANNULA

[75] Inventor: George B. Ogle, II, Alta Loma, Calif.

[73] Assignee: IMS, Limited dba International Medication Systems Limited, South El Monte, Calif.

[21] Appl. No.: 74,721

[22] Filed: Jul. 17, 1987

[51] Int. Cl.⁴ .............................................. A61M 5/32
[52] U.S. Cl. ................................... 604/192; 604/263; 604/86
[58] Field of Search ............... 604/192, 197, 198, 263, 604/160, 87, 86, 283, 80–86

[56] References Cited

U.S. PATENT DOCUMENTS

| | | | |
|---|---|---|---|
| 4,005,710 | 2/1977 | Zeddies et al. | 604/86 |
| 4,121,585 | 10/1978 | Becker, Jr. | 604/86 |
| 4,232,669 | 11/1980 | Nitshke | 604/192 |
| 4,392,499 | 7/1983 | Towse | 604/283 |
| 4,419,098 | 12/1983 | Bennett | 604/263 |
| 4,516,967 | 5/1985 | Kopfer | 604/87 |

Primary Examiner—John D. Yasko
Attorney, Agent, or Firm—Christie, Parker & Hale

[57] ABSTRACT

A protective device for enclosing the scarf of a cannula carried by a boss while permitting access to the said scarf by a port of a Y-site which is located into proximity to an adjoining length of flexible tubing forming part of an intravenous administration set. The protective device has a cylindrical sheath portion surrounding the cannula, the ends of the cylindrical portion having at least one cutout which snugly receives the flexible tubing.

4 Claims, 2 Drawing Sheets

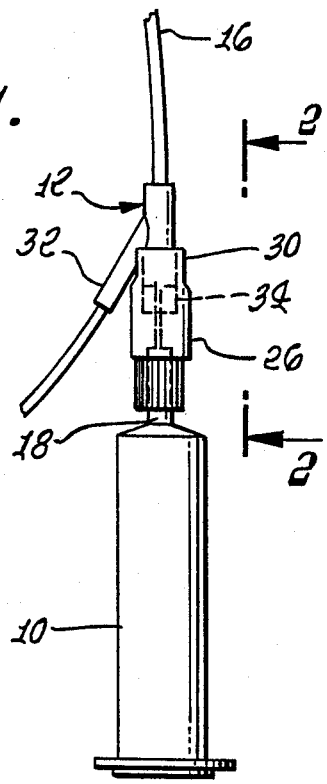
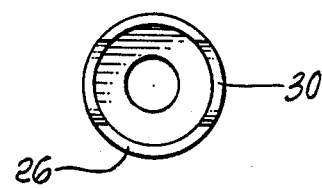
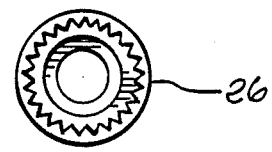
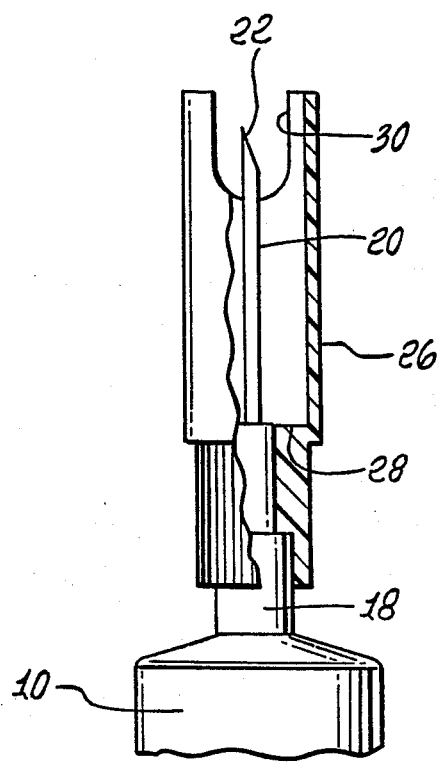
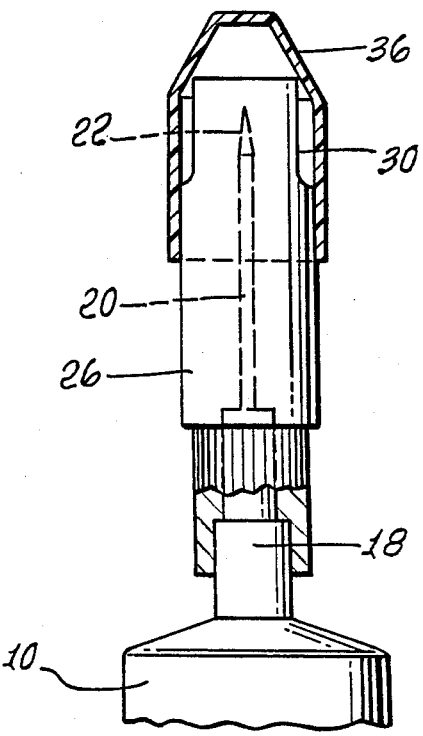

PROTECTED CANNULA

BACKGROUND OF THE INVENTION

The most frequent arrangement for the administration of parenteral drugs to a patient involves the use of an intravenous or giving set. In its simplest form an intravenous administration set is a length of tubing, one end of which is provided with a fitting for making connection to the stopper or outlet port of a bottle or flexible bag of intravenous solution, and the other end being provided with a needle, the scarf of which is adapted to be positioned within the vein of the patient. The set is otherwise provided with means to control flow rate and the like which are not relevant to the topic at hand.

In more recent years, it has become commonplace to infuse two intravenous solutions concurrently. This procedure is often referred to as "piggybacking". In order to permit piggybacking, intravenous administration sets are now provided with so-called Y-sites, the Y-site affording a second site for connection to the second source of intravenous solution. The Y-site is also commonly used as the place of injection of parenteral drugs in bolus form by pushing the drug from a hypodermic syringe through the Y-site and into the patient.

The problem addressed by the present invention arises from the occurrence of the acquired immune deficiency syndrome (AIDS) crises. The making of Y-site connections involves a number of manual including digital operations, often done in haste or under awkward circumstances. These manual procedures have frequently resulted in inadvertent needle punctures to nurses, physicians and technicians. In the past, such punctures of a minor consequence, represented little more than an inconvenience to the involved personnel. However, with the onset of the AIDS crises, this inconvenience has taken on a far more ominous nature, carrying with it the exposure of hospital personnel to the risk of contracting AIDS.

The present invention is addressed to reducing and eliminating this risk by means of a novel arrangement at the Y-site as more fully hereinafter described. It is believed that this invention makes an important contribution to the art and will be widely adopted by health care institutions and personnel.

SUMMARY OF THE INVENTION

Briefly, the present invention comprises the combination of:

an intravenous administration set having a Y-site, tubing extending therefrom having a patient-indwelling terminus, a second length of tubing extending from the Y-site with a terminal means for connection to a first source of intravenous solution, said Y-site having an inlet port adapted to be punctured by the scarf of a cannula for introduction of a second intravenous solution from a container or a parenteral injection by means of a hypodermic syringe; and a protective device positioned around a cannula which is adapted to communicate the contents of the intravenous solution container or hypodermic syringe with the tubing leading to the patient and adapted to abut the exterior of said Y-site, said protective device having a generally cylindrical portion surrounding the cannula over its length and extending beyond the end of the scarf of the needle, said cylindrical portion having at least one, and preferably two diametrically disposed cutouts, each adapted to snugly receive by lateral reception the tubing of the intravenous set while said scarf has punctured the said inlet port, said cannula being carried by a boss;

whereby the user, in making said combination, is protected by said cylindrical portion from inadvertent puncture of the hands and fingers by said scarf.

An object of this invention is to provide a novel protective device.

It is an object of this invention to provide important safeguards in the use of intravenous administration sets having Y-sites.

It is an object of my invention to provide a novel protective device which is effective in limiting and eliminating the risk of inadvertent puncture of the skin of providers of intravenous administration sets to patients.

It is a related object of my invention to increase the safety of using piggyback set-ups in the infusion of intravenous drugs and the bolusing of injectible drugs.

Specifically, it is an important object of this invention to provide a safeguard against the exposure of health care personnel to the risk of contracting AIDS through inadvertent skin punctures.

These and other objects of my invention will be apparent from the detailed description which follows, taken with the accompanying drawings.

DESCRIPTION OF THE PREFERRED EMBODIMENTS

Turning to the drawings:

FIG. 1 is a side view of one embodiment of my invention showing the protective device used with a hypodermic syringe at the Y-site of an intravenous administration set.

FIG. 2 is an enlarged view, in partial breakaway, taken from the perspective indicated by the line 2—2 in FIG. 1.

FIG. 3 is similar to FIG. 2 showing a modified protective device with a removable cover over the open end.

FIG. 4 is a top view of the structure shown in FIG. 2.

FIG. 5 is a bottom view of the structure shown in FIG. 2.

Figure 6:
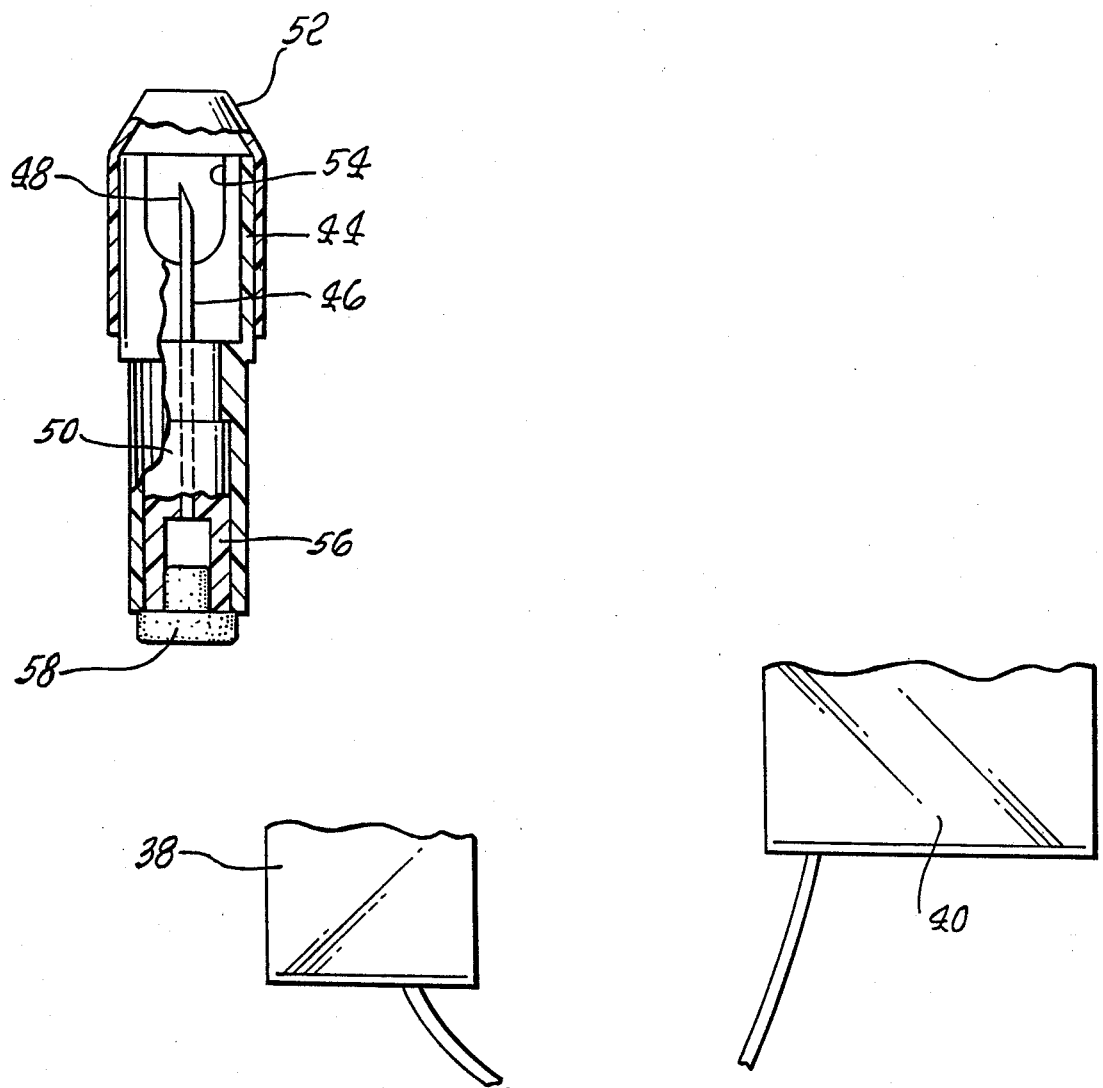
FIG. 6 is an alternative embodiment of the protective device of this invention, in side, partial sectional view, which is adapted to serve as a connection between a tubing leading to the set source of intravenous solution and the Y-site of an intravenous administration set.

Considering the drawings in more detail, FIGS. 1 to 5 show one preferred embodiment where a hypodermic syringe 10 containing a parenteral drug is being pushed or bolused into the patient at the Y-site (generally 12) of an intravenous set. The tubing 14 leads to a conventional flexible bag or bottle of intravenous solution commonly infused or dripped into a patient. The tubing portion 16 leads to the patient.

The construction of I.V. sets provided with Y-sites, as well as the configuration of flexible I.V. bottles and bags, is exceedingly well-known, and no useful purpose would be served by description of these elements. The syringe I.V. is provided with a boss 18 carrying cannula 20 having a sharpened outer end or scarf 22. The syringe barrel in the embodiment shown has a plunger 24 not shown. Other syringe and vial injector devices are known, and their use is, of course, within the scope of my invention. The vial injector of Ogle U.S. Pat. No. 3,376,866 is an example, and the disclosure of said patent is incorporated at this point by reference. All of these devices for bolusing parenteral drugs are referred to herein as a "hypodermic syringe".

The protective device is a generally cylindrical sheath 26 forming a closed end 28 by seal or integral formation with boss 18 of the syringe. If the sheath is not integral with the syringe it can be removable by a slip interference fit on the boss.

In such case, the sheath 26 terminates in an open end which is disposed beyond the end of scarf 22 of cannula 20 so that the health care provider is protected against inadvertent puncture. This important feature is best shown in FIG. 2 where the Y-site per se has been deleted in the interest of clarity of depiction.

The sheath 26 preferably has two diametrically disposed cutouts 30. One cutout is actually sufficient, but two cutouts provide greater convenience to the users. The dimensions of cutouts 30 are such as to accommodate the tubular Y-site portion 12 shown in FIG. 1, with portion 32 fitting fairly snugly in the cutout 30.

The Y-site has an injection site 34 having an imperforate closure or diaphragm which is pierced or punctured by scarf 22 concurrently with the tubular portion 32 being received in one or the other of said cutouts 30.

In this way, the contents of the syringe can be bolused into the patient via the Y-site in the usual way, with the important difference being that the health care provider is not apt to suffer an accidental needle puncture in the process of manually manipulating the syringe and Y-site to make the necessary connection to hook-up.

Prior to use, the sheath can be provided with a removable cap or cover 36 forming an aseptic seal with said sheath 26, as shown in FIG. 3.

The syringe can be, and preferably should be, thrown away without recapping to avoid unnecessary exposure to hazard.

Figure 7:
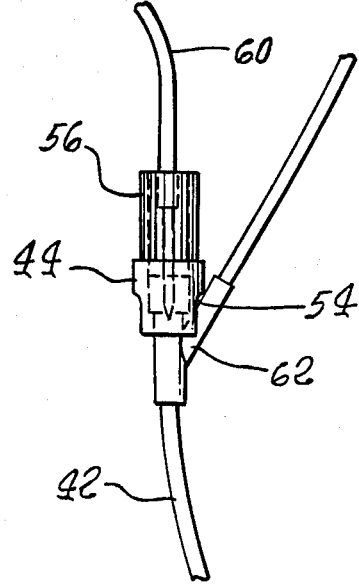
FIG. 7 is a perspective view showing the use of the protective device of FIG. 6 in place at the Y-site with the two intravenous solution containers being in a piggyback arrangement, the lower tubing leading to the patient.

An important alternate embodiment is shown in FIGS. 6 and 7 which involves the application of the present invention to the piggyback administration of two different containers 38 and 40 of I.V. solution. The tubing portion 42 leads to the patient. In this embodiment, the protective device of this invention comprises sheath 44, cannula 46, scarf 48, boss 50, cap 52, and cutouts 54. The sheath and boss are shown as separate pieces for convenience of manufacture, but could also be formed as a single integral element. The difference is that the side of the boss 50 opposite that from which cannula 46 projects has a cylindrical projection 56 with an open end sealed by removable plug 58. At the time of assembly of the piggyback of FIG. 7, plug 58 is discarded, and the tubular portion 60 leading to I.V. container 38 is inserted into projection 56 to form a fluid-tight seal. The sheath 44 and cutout 54 joins with the Y-site 62 in the same manner as previously described. The health care provider making this set-up is continuously protected against the hazard of an unwanted hand or finger puncture by inadvertent contact with scarf 48.

Having fully described the invention, it is intended that it be limited solely by the lawful scope of the appended claims.

I claim:

1. The combination of an intravenous administration set having a Y-site, a first tubing extending therefrom and adapted to connect to a patient-indwelling terminus, a second length of tubing extending from said Y-site with a terminal means adapted to be connected to a first source of intravenous solution, said Y-site having an inlet port, a hypodermic syringe adapted to hold a second intravenous solution, the syringe having a cannula with a scarf at one end, said cannula being carried by a boss spaced from the scarf; and a protective device carried by said hypodermic syringe and positioned around said cannula, said cannula connecting the interior of the hypodermic syringe with the tubing leading to the patient indwelling terminus, said protective device having a generally cylindrical sheath portion having a first open end and surrounding said cannula over its length and extending beyond the scarf end of said cannula at the first open end of said sheath, said sheath being affixed at its other end to said boss, said cylindrical portion having at least one cutout at said first open end which snugly receives, by lateral reception, one of the tubings of said intravenous administration set, while said scarf has punctured the said inlet port of said Y-site; whereby the user, in making said combination, is protected by the sheath of said protective device from inadvertent puncture of the hands and fingers by said scarf.

2. The combination of claim 1 wherein said cylindrical portion of said protective device has diametrically disposed cutouts, each adapted to snugly receive, by lateral reception, one of the tubings of the intravenous administration set while said scarf has punctured the said inlet port.

3. The combination of an intravenous administration set having a Y-site, a first tubing extending therefrom an adapted to be connected to a patient-indwelling terminus, a second length of tubing extending from said Y-site with a terminal means adapted to be connected to a first container of intravenous solution, said Y-site having an inlet port; and a protective device including a boss carrying a cannula with a scarf at one end spaced from the boss, said cannula being adapted to connect the contents of a second intravenous solution container with the tubing leading to the patient-indwelling terminus, said protective device having a generally cylindrical sheath portion having a first open end and surrounding the cannula over its length and extending beyond the scarf end of the cannula at the first open end of said sheath, said sheath being affixed at its other end to said boss, said cylindrical portion having at least one cutout at said open end which snugly receives, by lateral reception, one of the tubings of the intravenous administration set, while said scarf has punctured the said inlet port, whereby the user, in making said combination, is protected by said cylindrical portion from inadvertent puncture of the hands and fingers by said scarf.

4. The combination of claim 3 wherein said cylindrical portion of said protective device has diametrically disposed cutout, each adapted to snugly receive, by lateral reception, one of the tubings of the intravenous administration set while said scarf has punctured the said inlet port.

* * * * *

UNITED STATES PATENT AND TRADEMARK OFFICE
CERTIFICATE OF CORRECTION

PATENT NO.  : 4,834,716

DATED       : May 30, 1989

INVENTOR(S) : GEORGE B. OGLE, II

It is certified that error appears in the above-identified patent and that said Letters Patent is hereby corrected as shown below:

Col. 3, line 1, delete "24"
Column 3, line 2, change "not shown" to -- (not shown) --

Col. 4, line 39, change "an" to -- and --

Signed and Sealed this

Fifth Day of June, 1990

Attest:

HARRY F. MANBECK, JR.

*Attesting Officer*     *Commissioner of Patents and Trademarks*